United States Patent [19]

Ibragimov et al.

[11] Patent Number: 5,059,717

[45] Date of Patent: Oct. 22, 1991

[54] METHOD FOR PURIFICATION OF 2,2'-DI(1,6,7-TRIHYDROXY-3-METHYL-5-ISOPROPYL-8-NAPHTHALDEHYDE)

[76] Inventors: Bakhtiyar T. Ibragimov, 3 proezd Ilyasova, 7; Samat A. Talipov, massiv Junusabad, kvartal 15, 31, kv. 98; Rustam G. Mardanov, ulitsa Gvardii polkovnika Khodzhaeva, 15; Takhir F. Aripov, ulitsa Parashjutny gorodok, 8, all of Tashkent, U.S.S.R.

[21] Appl. No.: 552,342

[22] Filed: Jul. 16, 1990

Related U.S. Application Data

[63] Continuation of Ser. No. 293,826, Jan. 5, 1989, abandoned.

[51] Int. Cl.$^5$ .............................................. C07C 45/00
[52] U.S. Cl. ................................................... 568/438
[58] Field of Search ......................................... 568/438

[56] References Cited

PUBLICATIONS

Kadan et al. Cereal Chem. 55 (6): 916–926, 1978.
Campbell et al. J. A. C. S. 59 (5) pp. 1723–1728, 1937.

Primary Examiner—Bruce Gray
Attorney, Agent, or Firm—Burgess, Ryan & White

[57] ABSTRACT

The method according to the present invention comprises purification of 2,2'-di-(1,6,7-trihydroxy-3-methyl-5-isopropyl-8-naphthaldehyde) by crystallization from a solution thereof in diethyl ether with a concentration of 0.002–0.2 g/ml by adding 0.25–3 parts of hexane by volume (of diethyl ether) keeping the mixture at a temperature of from 10° to 30° C., separation of the resulting precipitate and drying thereof to give the desired product.

1 Claim, No Drawings

METHOD FOR PURIFICATION OF 2,2'-DI(1,6,7-TRIHYDROXY-3-METHYL-5-ISOPROPYL-8-NAPHTHALDEHYDE)

This application is a continuation of application Ser. No. 293,826, filed Jan. 5, 1989 now abandoned.

FIELD OF THE INVENTION

The present invention relates to the art of organic chemistry and, more specifically, to a method for purification of 2,2'-di-(1,6,7-trihydroxy-3-methyl-5-isopropyl-8-naphthaldehyde) which is useful as an active principle for pharmaceutical preparations possessing antitumor, antiviral, immunosuppressive and antifertile effects.

BACKGROUND OF THE INVENTION 2,2'-di-(1,6,7-trihydroxy-3-methyl-5-isopropyl-8-naphthaldehyde) or so-called gossypol is produced from the bark of cotton roots or from a by-product of processing of cotton seeds. Various pharmaceutical preparations have been developed on the basis of 2,2'-di-(1,6,7-trihydroxy-3-methyl-5-isopropyl-8-naphthaldehyde). In particular, in the form of a 3% liniment it is employed for the treatment of viral diseases of the skin and mucous membranes, as well as keratoconjunctivites.

Known in the art is a method for purification of 2,2'-di-(1,6,7-trihydroxy-3-methyl-5-isopropyl-8-naphthaldehyde) by crystallization thereof from an organic solvent, separation of the formed crystalline precipitate and drying thereof to give the desired product (Journal of the American Chemical Society, vol. 59, No. 5, 1937 /K. N. Campbell, R. C. Morris, R. Adams "The Structure of Gossypol I", p. 1723-1728).

According to this method, 2,2'-di-(1,6,7-trihydroxy-3-methyl-5-isopropyl-8-naphthaldehyde) is dissolved in diethyl ether, an equal volume of petroleum ether added at a temperature of from 30° to 60° C., concentrated under vacuum at 20° C. until the beginning of the formation of a crystalline residue. Then petroleum ether is added again and the mixture is allowed to stand for one hour. The residue is filtered-off and dried to give the desired product. The resulting 2,2'-di-(1,6,7-trihydroxy-3-methyl-5-isopropyl-8-naphthaldehyde) is used in the pharmaceutical industry.

However, the toxicity of 2,2'-di-(1,6,7-trihydroxy-3-methyl-5-isopropyl-8-naphthaldehyde) purified by this method is not always stable. It can surpass the allowable rated values which complicates the use of this compound in compositions of pharmaceutical preparations.

Also known is a method for purification of 2,2'-di-(1,6,7-trihydroxy-3-methyl-5-isopropyl-8-naphthaldehyde) by way of crystallization thereof from an organic solvent, separation of the resulting crystalline residue and drying thereof to give the desired product (SU, A, 1351915).

In this method gossypolacetic acid is dissolved in acetone. The solution is added with activated carbon and stirred for 10-15 minutes. The carbon is filtered-off and washed with acetone on the filter. The filtrate is heated to a temperature of 50°-55° C. and water heated to 55°-60° C. is slowly added thereto under stirring. Two hours thereafter the resulting fine-crystal precipitate is filtered-off, washed with water and dried in vacuum at the temperature of 60° C. for 6 hours to give 2,2'-di-(1,6,7-trihydroxy-3-methyl-5-isopropyl-8-naphthaldehyde) acceptable for use in medical practice.

However, the toxicity of 2,2'-di-(1,6,7-trihydroxy-3-methyl-5-isopropyl-8-naphthaldehyde) purified by this method is also unstable and can surpass the allowable rated values.

SUMMARY OF THE INVENTION

It is an object of the present invention to produce a stable purified compound 2,2'-di-(1,6,7-trihydroxy-3-methyl-5-isopropyl-8-naphthaldehyde) with a lowered toxicity.

This object is accomplished by providing a method for purification of 2,2'-di-(1,6,7-trihydroxy-3-methyl-5-isopropyl-8-naphthaldehyde) by way of crystallization thereof from an organic solvent, separation of the resulting crystalline residue and drying thereof to give the desired product, according to the present invention, the crystallization is conducted from a solution of 2,2'-di-(1,6,7-trihydroxy-3-methyl-5-isopropyl-8-naphthaldehyde) in diethyl ether with a concentration of 0.02-0.2 g/ml to which hexane is added in an amount of from 0.25 to 3 parts by volume of diethyl ether and the resulting mixture is maintained at a temperature within the range of from 10° to 30° C. till completion of the crystallization process.

The method for purification of 2,2'-di-(1,6,7-trihydroxy-3-methyl-5-isopropyl-8-naphthaldehyde) makes it possible to obtain a stable purified product with a lowered toxicity, since it enables its isolation in the form of an individual crystalline modification exhibiting a lowered toxicity.

DETAILED DESCRIPTION OF THE INVENTION

The method according to the present invention is performed in the following manner.

2,2'-di-(1,6,7-trihydroxy-3-methyl-5-isopropyl-8-napthaldehyde) is dissolved in diethyl ether to a concentration of 0.02-0.2 g/ml, and hexane added in an amount of from 0.25 to 3 parts by volume of diethyl ether and the resulting mixture is kept at a temperature within the range of from 10° to 30° C. till completion of the crystallization process. Then the resulting precipitate is separated and dried to give the desired product.

If a concentration of the solution of 2,2'-di-(1,6,7-trihydroxy-3-methyl-5-isopropyl-8-naphthaldehyde) in diethyl ether is above 0.2 g/ml, an amorphous phase will appear in the desired product.

If a concentration of the solution of 2,2'-di-(1,6,7-trihydroxy-3-methyl-5-isopropyl-8-naphthaldehyde) in diethyl ether is below 0.02 g/ml, the addition of hexane (in an amount of from 0.25 to 3 parts by volume of diethyl ether) will result in an extremely low yield of an individual crystalline form of gossypol.

If hexane is added to the solution of 2,2'-di-(1,6,7-trihydroxy-3-methyl-5-isopropyl-8-naphthaldehyde) in diethyl ether in an amount above 3 parts by volume of diethyl ether, a mixture of crystalline and amorphous phases will be formed in the desired product.

The same will occur upon keeping the mixture obtained after the addition of hexane at a temperature below 10° C.

When a mixture obtained after the addition of hexane is kept at a temperature above 30° C., due to an intensive evaporation of diethyl ether the concentration of 2,2'-di-(1,6,7-trihydroxy-3-methyl-5-isopropyl-8-napthaldehyde) in diethyl ether will be above 0.2 g/ml and, hence, as it has been already mentioned hereinabove, an amorphous phase will appear in the desired product.

If to a solution of 2,2'-di-(1,6,7-trihydroxy-3-methyl-5-isopropyl-8-napthaldehyde) in diethyl ether is added hexane in an amount lesser than 0.25 part by volume of diethyl ether, the yield of the individual crystalline form is very low.

For a better understanding of the present invention, some specific examples are given hereinbelow by way of illustration.

EXAMPLE 1

1 g of 2,2'-di-(1,6,7-trihydroxy-3-methyl-5-isopropyl-8-naphthaldehyde) is dissolved in 5 ml of diethyl ether, 15 ml of hexane added and maintained at a temperature of 17°-18° C. till completion of precipitation. The resulting precipitate is filtered-off and dried in vacuum to give the desired product. An individual crystalline modification of 2,2'-di-(1,6,7-trihydroxy-3-methyl-5-isopropyl-8-naphthaldehyde) is obtained with the following crystallographic parameters; $a=20.721$ (5) Å; (b=26.018 (4) Å; $c=27.957$ (5) Å; $\gamma=96.83$ (2) Å; $V=14,965$ (5) Å$^3$; steric group B 2/b.

The results of tests for an acute toxicity of the thus-obtained desired product when administered orally to mice are shown in the Table hereinbelow.

EXAMPLE 2

1 g of 2,2'-di-(1,6,7-trihydroxy-3-methyl-5-isopropyl-8-naphthaldehyde) is dissolved in 50 ml of diethyl ether, 50 ml of hexane added and kept at a temperature of 28°-30° C. till completion of precipitation.

The resulting crystalline precipitate is filtered-off and dried under vacuum to give the desired product. An individual crystalline modification of 2,2'-di-(1,6,7-trihydroxy-3-methyl-5-isopropyl-8-naphthaldehyde) is obtained with the following crystallographic parameters: $a=13.467$ (I) Å; $b=8.794$ (I) Å; $c=21.376$ (3) Å; $\gamma=97.22$ (I) Å; $v=2,511$ (0.5) Å$^3$; steric group P 2$_1$/b.

The results of tests of the thus-obtained desired product for an acute toxicity in oral administration to mice are shown in the Table hereinbelow.

EXAMPLE 3

1 g of 2,2'-di-(1,6,7-trihydroxy-3-methyl-5-isopropyl-8-naphthaldehyde) is dissolved in 20 ml of diethylether 5 ml of hexane, added and the resulting mixture is allowed to stand at a temperature of 10°-12° C. till completion of precipitation. The obtained crystalline precipitate is filtered-off and dried under vacuum to give the desired product.

An individual crystalline modification of 2,2'-di-(1,6,7-trihydroxy-3-methyl-5-isopropyl-8-naphthaldehyde) is thus obtained with the following crystallographic parameters: $a=8.557$ (2) Å; $b=14.474$ (5) Å; $c=25.651$ (5) Å; $=\beta 107.22$ (2) Å; $v=3,035$ (2) Å; steric group P 2$_1$/c.

The results of tests of the thus-obtained desired product for an acute toxicity are shown in the Table hereinbelow.

TABLE

Acute toxicity of 2,2'-di-(1,6,7-trihydroxy-3-methyl-5-isopropyl-8-naphthaldehyde) in oral administration to mice

| No | Product of | LD$_{50}$,mg/kg |
|---|---|---|
| 1 | Example 1 | 640 (450–768) |
| 2 | Example 2 | over 1,500 |
| 3 | Example 3 | 750 (646–870) |
| 4 | known preparation (SU,A,1351915) | 383 (340–426) |

What is claimed is:

1. A method for purification of 2,2'-di(1,6,7-trihydroxy-3-methyl-5-isopropyl-8-naphthaldehyde) by crystallization of said 2,2'-di-(1,6,7-trihydroxy-3-methyl-5-isopropyl-8-naphthaldehyde) from a solution thereof in diethyl ether, which comprises the steps of:
   1) preparing a solution containing 0.2–0.2 g/ml of said naphthaldehyde in diethyl ether,
   1) adding hexane to said solution in an amount of 0.25–3 parts by volume per part of diethyl ether,
   3) maintaining said solution at a temperature of from 10° to 30° C. until crystallization is complete, and
   4) separating and drying the resulting crystalline precipitate.